US 8,399,246 B2

(12) United States Patent
Hu et al.

(10) Patent No.: US 8,399,246 B2
(45) Date of Patent: Mar. 19, 2013

(54) BACULOVIRUS EXPRESSION VECTOR AND METHOD THEREWITH FOR GENERATING IMMUNOGENICITY IN A HOST

(75) Inventors: Yu-Chen Hu, Hsinchu (TW); Chi-Yuan Chen, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 514 days.

(21) Appl. No.: 12/574,450

(22) Filed: Oct. 6, 2009

(65) Prior Publication Data

US 2011/0045540 A1 Feb. 24, 2011

(30) Foreign Application Priority Data

Aug. 18, 2009 (TW) ................................. 98127683 A (51) Int. Cl.
*C12N 15/00* (2006.01)

(52) U.S. Cl. .................. 435/320.1; 435/235.1; 536/24.1

(58) Field of Classification Search ........................ None
See application file for complete search history.

(56) References Cited

U.S. PATENT DOCUMENTS

| 7,714,119 | B2 * | 5/2010 | Fang et al. | ................. | 536/23.53 |
| 8,080,255 | B2 * | 12/2011 | Smith et al. | ................ | 424/210.1 |
| 2008/0003203 | A1 | 1/2008 | Hu et al. | | |

OTHER PUBLICATIONS

Tami et al., Arch. Virol., vol. 145, pp. 1815-1828 (2000).*

* cited by examiner

*Primary Examiner* — Jim Ketter
(74) *Attorney, Agent, or Firm* — Muncy, Geissler, Olds & Lowe, PLLC (57) ABSTRACT

A baculovirus expression vector achieves dual functions of (1) subunit vaccine by displaying the influenza surface protein for humoral immune responses; and (2) DNA vaccine by expressing influenza surface protein for long-acting cellular immune response. A method for inducing immunogenicity in a host is also disclosed.

6 Claims, 9 Drawing Sheets

BACULOVIRUS EXPRESSION VECTOR AND METHOD THEREWITH FOR GENERATING IMMUNOGENICITY IN A HOST

BACKGROUND OF THE INVENTION

1. Field of the Invention

The present invention relates to a baculovirus expression vector and method therewith for generating immunogenicity in a host, particularly to a baculovirus expression vector simultaneously displaying and expressing influenza surface protein and method therewith for generating immunogenicity in a host.

2. Description of the Prior Art

Influenza viruses, type A members of the Orthomyxoviridae family, have eight negative sense RNA segments encoding 10 proteins. Among these genes, the hemagglutinin (HA) and neuraminidase (NA) genes encode virulence-associated surface glycoproteins, are responsible for attachment of virus to terminal sialic acid residues on host cell receptors, and mediate fusion between viral and cellular membranes and detachment from infected cells. To date, viruses of 16 HA and 9 NA subtypes have been identified in avian species. Among the 16 HA subtypes, the highly pathogenic (HP) phenotypes are only associated with some strains of the H5 or H7 HA subtype.

Inactivated Vaccine

Because of high pathogenicity and high mortality of the new H5N1 avian influenza virus, novel vaccines must be developed to control and prevent its infection. Trivalent inactivated vaccine has now been used as the standard influenza vaccine and contains HA and NA of the present epidemic strain (usually two strains of influenza A and one strain of influenza B). The inactivated vaccine is prepared by inactivating the influenza virus produced in the chicken embryonated eggs with chemical reagents and extracting the necessary antigen protein for immunization by intramuscular injection. This method has been practiced for over 50 years and is still the mainstream manufacturing method of influenza vaccine for now. However, chicken embryonated eggs have some drawbacks for producing influenza vaccine. First, this method may not be used for manufacturing vaccine of high pathogenicity strains (e.g. H5N1) because they may be lethal to the eggs. The product manufactured by the method may also be unsuitable for those allergic to eggs. In addition, the inactivate vaccine has some drawbacks: (1) It induces effective neutralizing antibodies but elicits less potent cellular immune response such as cytotoxic T lymphocytes (CTL) that are required to eliminate infected cells, and hence confers less immune protection against virus and parasitized bacteria or parasites; (2) It fails to increase the generation of memory T cells and may require multiple booster injections to achieve vaccine efficacy.

Attenuated Vaccine

Attenuated vaccine, by definition, is attenuated for virus virulence but is still capable of transient growth and proliferation in vivo. The prolonged existence of attenuated vaccine in the host theoretically increases the possibility for the immune system to recognize the antigen to increase immunity and the generation of memory immune cells. The endogenous antigen expression in the host may also be an advantage for effective elicitation of cytotoxic T cells.

However, the attenuated vaccine has some drawbacks including:

(1) It is live and may revive, raising safety concerns.
(2) It may cause risks of infection for those having incompetent immune systems.
(3) It has to be produced at facilities with more stringent biosafety regulations, leading to more complicated procedures and higher cost.

To solve the above-mentioned problems, US Patent application No. 20080003203 disclosed a pseudotyped baculovirus vector which displays HA on its membrane to generate host immunogenicity against HA and thus may be developed as a vaccine for eliciting antibody reaction to neutralize influenza virus. However, the pseudotyped baculovirus vector may elicit only humoral immune responses, but fails to trigger long-lasting cellular immune response.

Therefore, it is now a current goal to develop a novel vaccine that elicits not only the humoral immune response but also the long-acting cellular immune response.

SUMMARY OF THE INVENTION

The present invention is directed to providing a baculovirus expression vector and method therewith for generating immunogenicity in a host to achieve dual functions of (1) subunit vaccine by displaying the influenza surface protein for humoral immune response; and (2) DNA vaccine by expressing influenza surface protein for long acting cellular immune response. A method for inducing immunogenicity in a host is also herein disclosed.

According to one embodiment, a baculovirus expression vector includes a first gene cassette and a second gene cassette. The first gene cassette includes a first influenza surface protein sequence encoding a first influenza surface protein, a baculovirus protein signal sequence, and a first promoter. The baculovirus protein signal sequence is operably linked to the 5' end of the first influenza surface protein sequence and encodes a baculovirus signal peptide, wherein the baculovirus signal peptide is linked to the N-terminal domain of the first influenza surface protein and is capable of membrane localization. The first promoter is operably linked to the first influenza surface protein sequence and the baculovirus protein signal sequence and drives the expression of the first influenza surface protein as the baculovirus replicates in the insect cells. The second gene cassette includes a second influenza surface protein sequence encoding a second influenza surface protein and a second promoter operably linked to the second influenza surface protein sequence and driving the expression of the second influenza surface protein in a host. The first influenza surface protein sequence and the second influenza surface protein sequence may respectively include a hemagglutinin (HA) or a neuraminidase (NA). The second promoter drives the second influenza surface protein sequence after the baculovirus is introduced into the host for expressing influenza surface protein in host cells.

According to another embodiment, a method for generating immunogenicity in a host includes amplifying and harvesting a baculovirus, wherein the baculovirus includes a first influenza surface protein sequence encoding a first influenza surface protein, a baculovirus protein signal sequence, and a first promoter. The baculovirus protein signal sequence is operably linked to the 5' end of the first influenza surface protein sequence and encodes a baculovirus signal peptide, wherein the baculovirus signal peptide is configured for membrane localization and linked to the N-terminal domain of the first influenza surface protein. The first promoter is operably linked to the first influenza surface protein sequence and the baculovirus protein signal sequence so as to drive the expression of the first influenza surface protein as the baculovirus replicates in the insect host. The baculovirus is then harvested and introduced into a host, wherein the baculovirus further includes a second influenza surface protein sequence encoding a second influenza surface protein and a second promoter operably linked to the second influenza surface protein sequence. The first influenza surface protein sequence and the second influenza surface protein sequence respectively include a hemagglutinin or a neuraminidase. After the baculovirus is introduced into the host, the second promoter drives the second influenza surface protein sequence for expressing influenza surface protein in host cells.

Other advantages of the present invention will become apparent from the following descriptions taken in conjunction with the accompanying drawings wherein are set forth, by way of illustration, example and certain embodiments of the present invention.

BRIEF DESCRIPTION OF THE DRAWINGS

The foregoing aspects and many of the accompanying advantages of this invention will become more readily appreciated as the same becomes better understood by reference to the following detailed descriptions, when taken in conjunction with the accompanying drawings, wherein.

DESCRIPTION OF THE PREFERRED EMBODIMENT

Construction of the Baculovirus Expression Vector

Figure 1A:
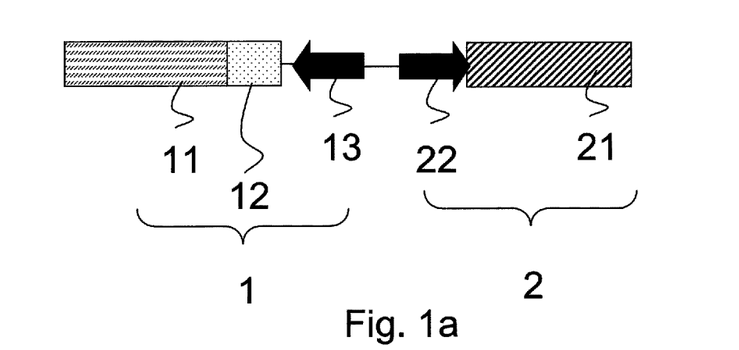
FIG. 1a is a schematic diagram illustrating a baculovirus expression vector according to one embodiment of the present invention.

Referring to FIG. 1a, in one embodiment, a baculovirus expression vector may be introduced into a host for generating immunogenicity in the host, including steps of amplifying and harvesting baculovirus, wherein the baculovirus includes a first influenza surface protein sequence 11 encoding a first influenza surface protein, a baculovirus protein signal sequence 12, and a first promoter 13. The baculovirus protein signal sequence 12 is operably linked to the 5' end of the first influenza surface protein sequence 11 and encodes a baculovirus signal peptide, wherein the baculovirus signal peptide is configured for membrane localization and linked to the N-terminal domain of the first influenza surface protein. The first promoter 13 is operably linked to the first influenza surface protein sequence 11 and the baculovirus protein signal sequence 12 so as to drive the expression of the first influenza surface protein as the baculovirus replicates in the insect cells. The harvested baculovirus is then introduced into a host, wherein the baculovirus further includes a second influenza surface protein sequence 21 encoding a second influenza surface protein and a second promoter 22 operably linked to the second influenza surface protein sequence 21. The first influenza surface protein sequence 11 and the second influenza surface protein sequence 21 respectively encode a hemagglutinin and/or a neuraminidase. After the baculovirus is introduced into the host, the second promoter 22 drives the influenza surface protein sequence 21 for expressing influenza surface protein in host cells.

Figure 1B:
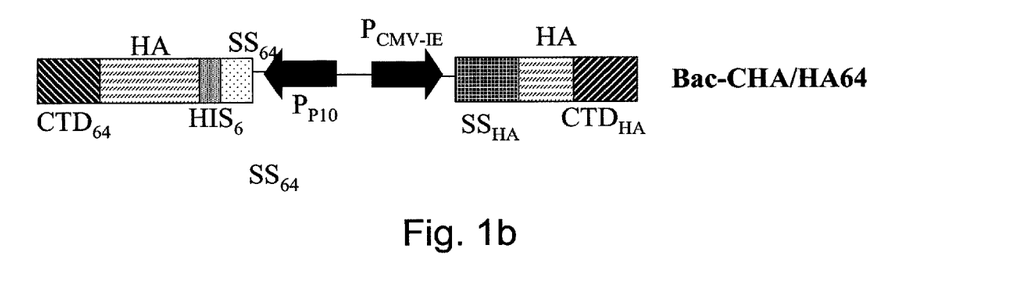
FIG. 1b is a schematic diagram illustrating another baculovirus expression vector according to one embodiment of the present invention.

Referring to FIG. 1b, in one embodiment, a recombinant baculovirus, Bac-CHA/HA64, is constructed and obtained by genetically engineering the pFastBac Dual™ vector commercially available from Gibco and configured for displaying and expressing hemagglutinin for improved vaccine efficacy. In addition, as illustrated in FIG. 1c, recombinant baculovirus Bac-HA64 of conventional art may only display HA.

Figure 1C:
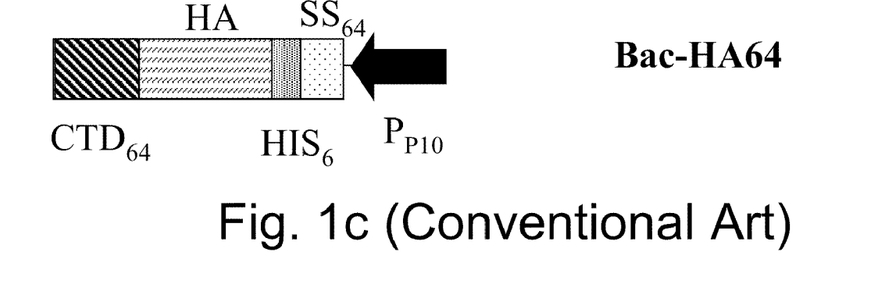
FIG. 1c is a schematic diagram illustrating another baculovirus expression vector of the conventional art.
Figure 1D:
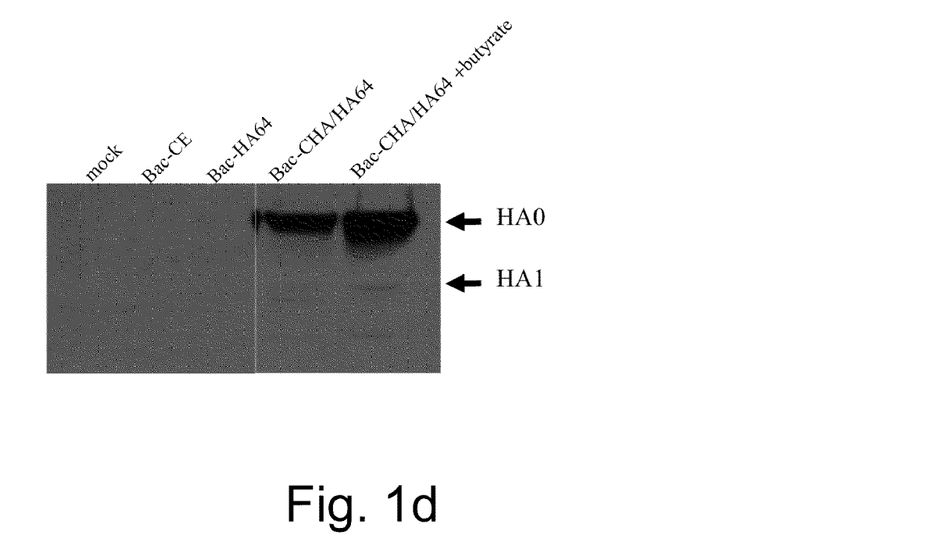
FIG. 1d is a diagram illustrating the experimental results according to one embodiment of the present invention.
Figure 2A:
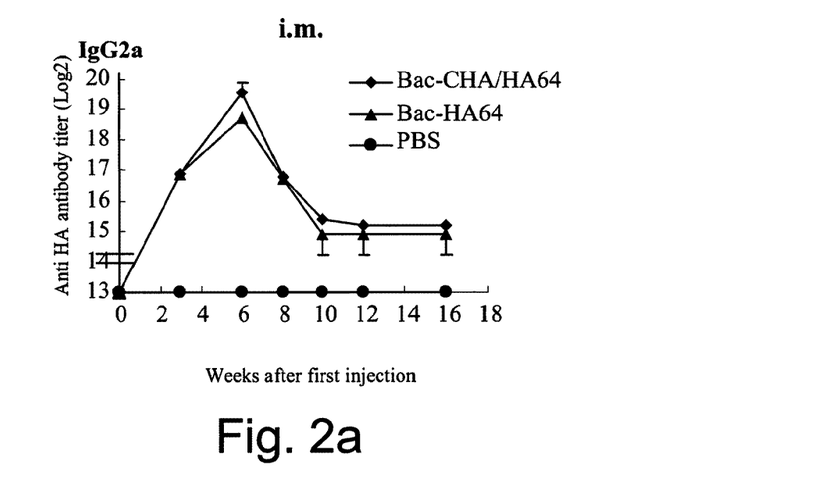
FIGS. 2a-2d are broken line graphs illustrating the experimental results according to one embodiment of the present invention.
Figure 2B:
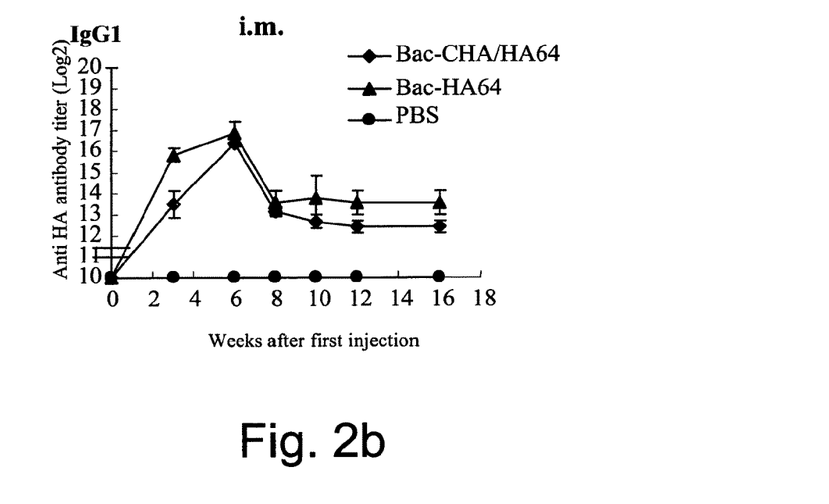
Figure 2C:
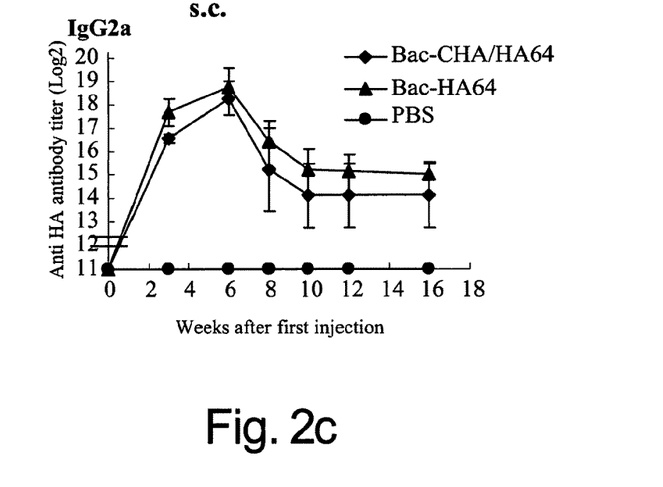
Figure 2D:
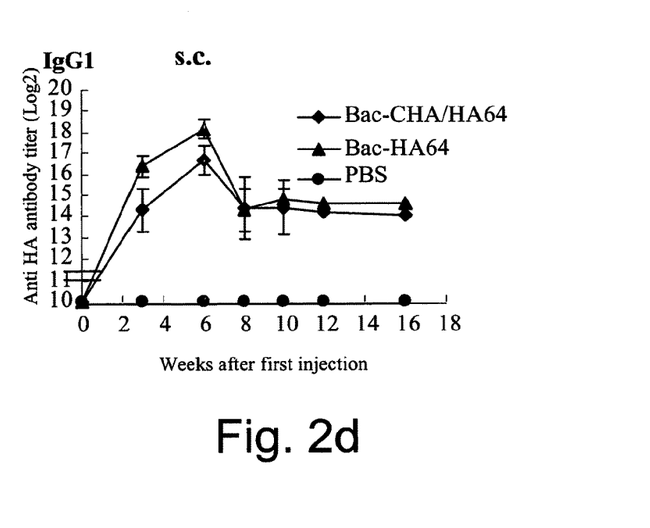
Figure 3A:
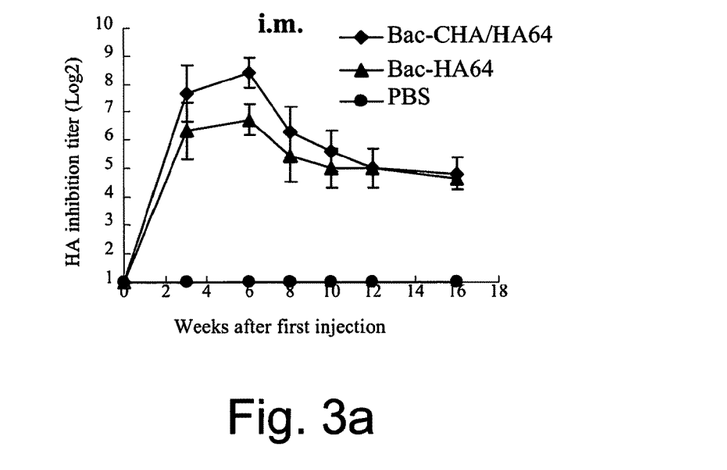
FIGS. 3a-3b are broken line graphs illustrating the experimental results according to one embodiment of the present invention.
Figure 3B:
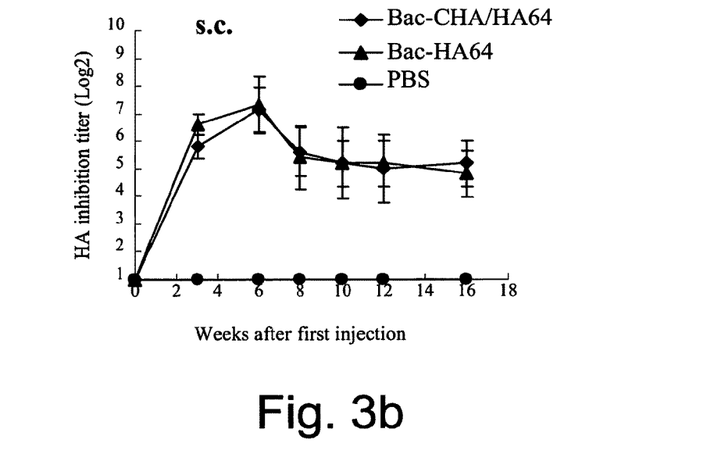
Figure 4:
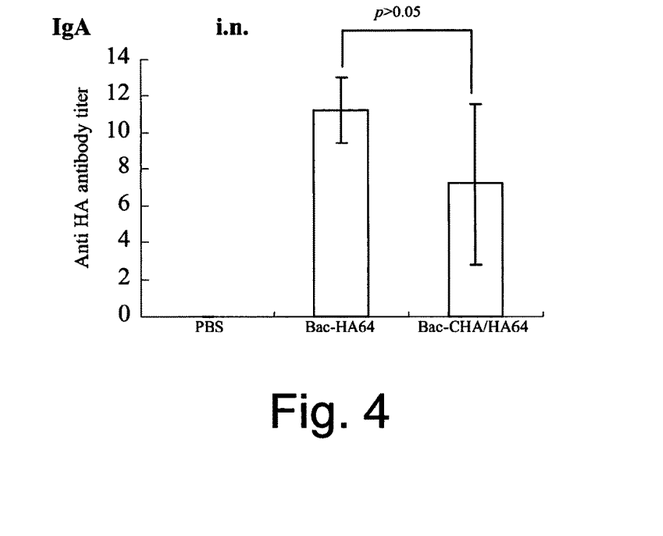
FIG. 4 is a bar chart illustrating the experimental results according to one embodiment of the present invention.
Figure 5A:
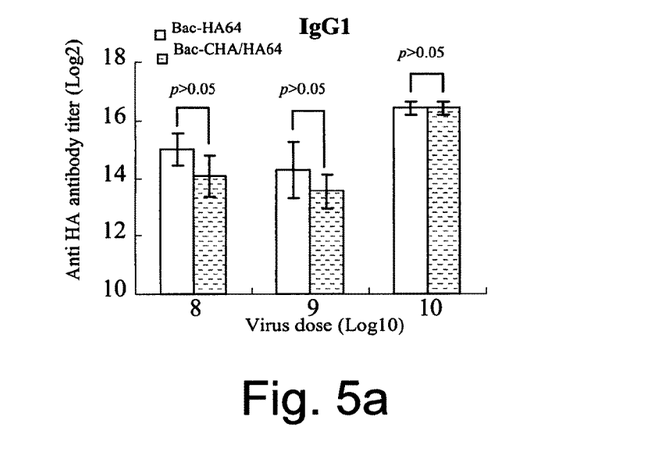
FIGS. 5a-5c are bar charts illustrating the experimental results according to one embodiment of the present invention.
Figure 5B:
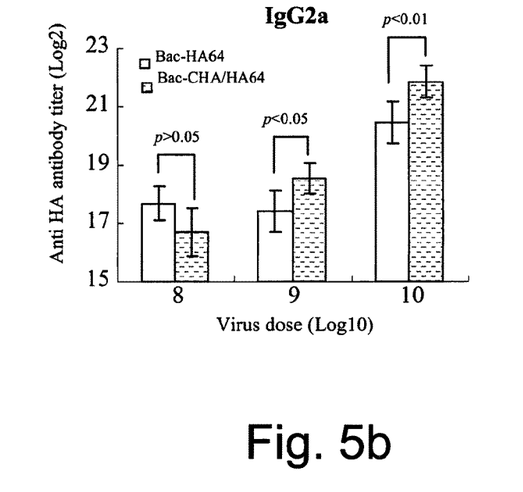
Figure 5C:
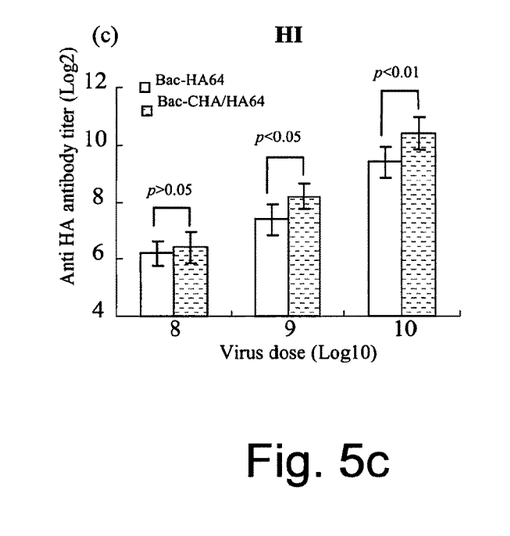

Referring to FIGS. 1b and 1c, Bac-CHA/HA64 and Bac-HA64 harbor a chimeric HA gene driven by the p10 promoter ($P_{p10}$). The 5' end of the HA gene may be replaced by a baculoviral gp64-derived signal sequence, $SS_{64}$. The 3' end of HA sequence encoding the HA may be replaced by $CTD_{64}$, which is the cytoplasmic domain (CTD) sequence originated from baculovirus envelope protein gp64. This design enables efficient chimeric HA expression in insect cells and subsequent incorporation into the baculoviral envelope.

Both Bac-CHA/HA64 and Bac-HA64 are recombinant baculoviruses that enable HA display and have the recombinant sequence including the sequence encoding the signal peptide of gp64 ($SS_{64}$), hemagglutinin sequence (HA) and the cytoplasmic domain sequence of gp64 ($CTD_{64}$). The signal peptide encoded by $SS_{64}$ enables the translocation of the expressed fusion protein onto the membrane of infected insect cells, and the cytoplasmic domain of gp64 encoded by $CTD_{64}$ has the ability to direct the incorporation of gp64 protein into the budding virion, resulting in the display of the fusion protein on the viral envelope. Baculovirus vectors can be designed to incorporate exogenous proteins into the viral envelope when specific signal peptide and carboxyl terminal domain of gp64 are expressed with the exogenous HA protein in form of fusion protein. When the appropriate fusion protein is expressed, the protein is translocated to the plasma membrane where it is incorporated into the viral envelope upon virus budding. The HA display is hence achieved with the above-mentioned mechanism in Bac-CHA/HA64 of the present invention and Bac-HA64.

This design enables the effective expression of fused hemagglutinin by HA sequence in infected insect cells and subsequent incorporation into the baculovirus envelope. Thanks to the surface expression on baculovirus, both baculovirus gene vectors Bac-HA64 and Bac-CHA/HA64 may elicit anti-HA antibody responses in the animal host to achieve the function of hemagglutination inhibition (HI) and function like a subunit vaccine.

Different from Bac-HA64, Bac-CHA/HA64 is designed to express HA under the control of cytomegalovirus immediate-early promoter ($P_{CMV-IE}$) for the endogenous HA expression in mammalian cells besides exogenous HA display. As illustrated in FIG. 1b, Bac-CHA/HA64 further contains another hemagglutinin sequence with authentic HA signal sequence ($SS_{HA}$) and cytoplasmic domain sequence ($CTD_{HA}$). After transducing mammalian or other cells whereby $P_{CMV-IE}$ is active, Bac-CHA/HA64 expresses HA under the transcriptional control of $P_{CMV-IE}$, which serves as an endogenous immunogen; thus Bac-CHA/HA64 functions like a DNA vaccine.

Therefore, Bac-CHA/HA64 contains two gene cassettes and achieves functions of (1) subunit vaccine as the pseudotyped baculovirus displaying HA; (2) DNA vaccine by transducing the animal (e.g. mammalian or avian) cells and expressing HA therein. Baculovirus Bac-CHA/HA64 may be amplified by infecting the insect cells, harvested and introduced into the host; therefore, the cost for manufacturing and purification may be lowered.

Furthermore, those skilled in this art may select any suitable promoters for the present invention. For example, the first promoter contains without limitations to p10 promoter, polyhedrin promoter, and so on. The second promoter for the mammalian contains without limits to $P_{CMV-IE}$, SV40 (Simian virus 40) promoter, human EF-1α, a CMV early enhancer/chicken β actin (CAG), and so on.

In one embodiment, a baculovirus expression vector of the present invention may be applicable in avian species with suitable promoters, e.g. $P_{CMV-IE}$. WSSV promoter (White spot syndrome virus immediate-early promoter one (ie1)), human alpha-1-anti-trypsin promoter, or SV40 promoter.

In addition, in this embodiment, the wild-type gp64 gene may be amplified by PCR and subcloned for constructing Bac-HA64 and Bac-CHA/HA64, thereby a stretch of 6 histidine residues (His 6 tag) is inserted between the signal sequence and the HA sequence; however, the present invention is not thus limited as such.

Display and Expression of Baculovirus Expression Vector

Bac-CHA/HA64 and Bac-HA64 contain identical gene cassettes for HA display and induction of syncytia formation after infection of insect cells. Syncytia formation is mediated by HA and is also observed after infection, indicating the HA display on the surface of Bac-CHA/HA64 (data not shown).

The HA expression in mammalian cells was verified by transducing BHK (baby hamster kidney) cells with Bac-CE (a baculovirus expressing EGFP (Enhanced Green Fluorescent Proteins), Bac-HA64 or Bac-CHA/HA64 at MOI 100, followed by Western blot analysis using the anti-HA antibody. FIG. 1*d* reveals no HA expression in the mock-transduced cells and the cells transduced with either Bac-CE or Bac-HA64, yet HA was expressed in the form of HA0 in the Bac-CHA/HA64-transduced cells.

In one embodiment, the expression levels were enhanced by the addition of sodium butyrate, a histone deacetylase inhibitor that enhances baculovirus-mediated expression, as illustrated in FIG. 1*d*.

Results of Humoral Immune Response

Immune responses in the host elicited by Bac-CHA/HA64 and Bac-HA64 are then evaluated.

To compare the humoral immune responses elicited by these vectors, female BALB/c mice (n=5 for each group) were vaccinated with PBS (MOCK group), Bac-HA64 or Bac-CHA/HA ($1\times10^9$ PFU/mouse) via intramuscular (i.m.), subcutaneous (s.c.) or intranasal (i.n.) routes.

After the primary injection, the mice received booster injections with the same dosage at weeks 2 and 4. The sera were collected at $3^{rd}$, $6^{th}$, $8^{th}$, $10^{th}$, $12^{th}$ and $16^{th}$ week, and analyzed by ELISA (Enzyme-linked immunosorbent assay) for anti-HA IgG2a and IgG1 titers, which correlated with the magnitudes of Th1 and Th2 responses, respectively. As expected, PBS injection elicited no IgG2a and IgG1 titers regardless of the administration routes (FIG. 2*a*-2*d*). I.n. administration resulted in fairly low IgG1 and IgG2a titers ($<2^{10}$), thus the data are not illustrated.

In contrast, i.m. and s.c. injection of either one of the 2 baculovirus vectors elicited IgG2a and IgG1 antibodies, whose titers culminated at 6 weeks post-immunization, declined thereafter but remained stable for at least 16 weeks (FIGS. 2*a*-2*d*). Via the i.m. route, Bac-CHA/HA64 led to similar peak IgG2a titers at week 6, which significantly exceeded that of Bac-HA64 (FIG. 2*a*). The IgG1 titer was similar for Bac-CHA/HA64 and Bac-HA64. Via the s.c. route, Bac-HA64 led to the highest IgG2a (FIG. 2*c*) and IgG1 (FIG. 2*d*) titers among the three groups (Bac-CHA/HA64, Bac-HA64, and PBS) from week 3 to week 16. In comparison with the s.c. administration, Bac-CHA/HA64 vaccinated via i.m. injection resulted in higher peak IgG2a titers, but lower peak IgG1 titers.

The HI titers were next measured in order to examine whether the antibodies were capable of hemagglutination inhibition. Concurrent with the IgG titer profiles, the i.m. (FIG. 3*a*) and s.c. (FIG. 3*b*) vaccination elicited HI titers that culminated at weak 6 and persisted for at least 16 weeks. Notably, i.m. injection by and large gave rise to higher HI titers than s.c. administration. Via the i.m. route, the HI titer during $3^{rd}$ week to $10^{th}$ week for Bac-CHA/HA64 was higher than that for Bac-HA64. Via the s.c. route, Bac-CHA/HA64 and Bac-HA64 led to similar HI titers.

Results of Mucosal Immunity

As mentioned above, i.n. administration elicited poor anti-HA IgG response. Since mucosal immunity plays an important role in preventing influenza virus from entering the nasal membrane, whether i.n. administration of baculovirus vectors triggered mucosal immune responses was explored. To this end, the mice were vaccinated with Bac-HA64 or Bac-CHA/HA64 ($1\times10^9$ PFU/mouse) via i.n. administration and the IgA titers in the BAL (bronchoalveolar lavage) were measured by ELISA.

FIG. 4 depicts that the PBS group induced no IgA, and Bac-HA64 and Bac-HA64/CHA elicited statistically similar ($p>0.05$) IgA titers. Therefore, via i.n. administration, Bac-HA64 and Bac-CHA/HA64 elicited similar mucosal immunity, but did not trigger significant humoral or cellular immune response.

Dosage Effect on the Immune Responses Induced by Baculovirus Vectors

The dosage effect on the immune responses was examined by immunizing the mice (5 mice/group) with each of baculovirus vectors at different doses ($1\times10^8$, $1\times10^9$ or $1\times10^{10}$ PFU/mouse) via the i.m route. The mice received booster injections at $2^{nd}$ and $4^{th}$ week as illustrated in FIG. 2 and the serum IgG1, IgG2a and HI titers were measured at $6^{th}$ week. FIG. 5*a* illustrates that the IgG1 titers were similar at $1\times10^8$ and $1\times10^9$ PFU/mouse, but were dramatically increased to 16.3 at $1\times10^{10}$ PFU/mouse. No significant differences in IgG1 titers existed between both vectors, regardless of the vector dose. With respect to IgG2a titers (FIG. 5*b*), there existed a clear dose response for the Bac-CHA/HA64 group, in particular the titers were dramatically elevated to 21.8 (Bac-CHA/HA64) at $1\times10^{10}$ PFU/mouse. Bac-HA64 gave similar IgG2a titers at $1\times10^8$ and $1\times10^9$ PFU/mouse but resulted in an IgG2a titer up to 20.4 at $1\times10^{10}$ PFU/mouse. The results in Table 1 were calculated from FIG. 5*a* and FIG. 5*b*. As illustrated in Table 1, the IgG2a/IgG1 ratio for Bac-CHA/HA64 increased from 6.5 to 44 as the viral dosage increased from $1\times10^8$ to $1\times10^{10}$ PFU/mouse. The ratios were higher than those induced by Bac-HA64 (6.2 to 18), indicating that Bac-CHA/HA64 elicits a stronger Th1 response than Bac-HA64 does.

TABLE 1

Different baculoviruses elicit different IgG2a/IgG1 ratios

| Dosage | IgG2a/IgG1 ratio | |
|---|---|---|
| (PFU/mouse) | Bac-HA64 | Bac-CHA/HA64 |
| $10^8$ | 6.2 | 6.5 |
| $10^9$ | 8 | 30 |
| $10^{10}$ | 18 | 44 |

As illustrated in FIG. 5*c*, the HI titers for both groups increased with virus dosage, demonstrating an apparent dose response. Bac-CHA/HA64 induced significantly higher HI titers than Bac-HA64 did at $10^9$-$10^{10}$ PFU/mouse ($p<0.05$).

Figure 6A:
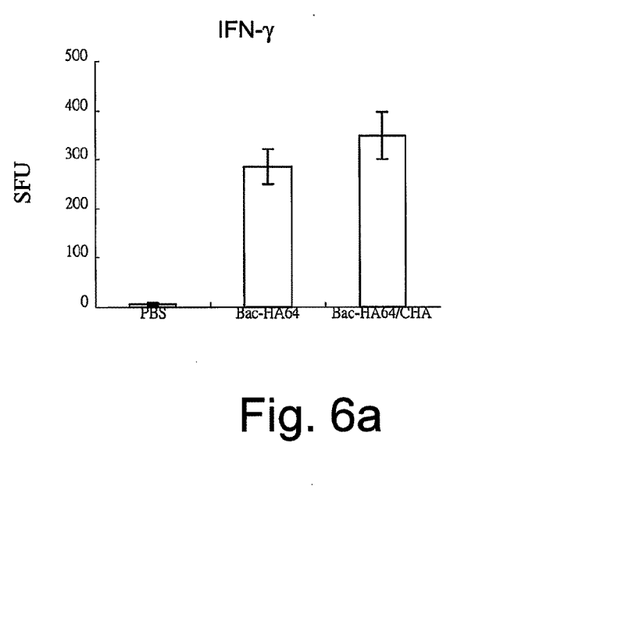
FIGS. 6a-6b are bar charts illustrating the experimental results according to one embodiment of the present invention.
Figure 6B:
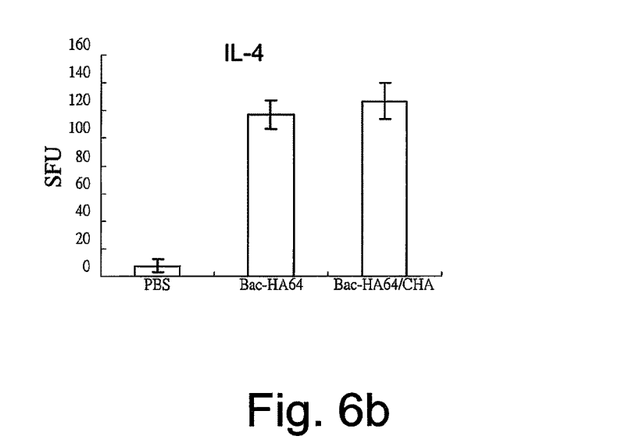

To assess the cellular immune responses, the mice were i.m. immunized with Bac-HA64 or Bac-CHA/HA64 at $1\times10^{10}$ PFU/mouse, and received booster injections at $2^{nd}$ and $4^{th}$ week. The splenocytes were harvested at $5^{th}$ week and the cytokines representative of Th1 (IFN-γ, interferon gamma) and Th2 (IL-4) responses were measured by ELISPOT (Enzyme-linked Immunospot Assay). FIG. 6a illustrates that Bac-CHA/HA64 induced more IFN-γ-secreting splenocytes (SFU (spot forming unit)≈398) than Bac-HA64. Conversely, Bac-HA64 (SFU≈117) and Bac-HA64/CHA (SFU≈127) led to similar IL-4 responses. Bac-CHA/HA64 induced higher numbers of IFN-γ-secreting splenocytes than the IL-4-secreting splenocytes for Bac-CHA/HA64, suggested a response more biased towards Th1 response instead of Th2 response.

Figure 7:
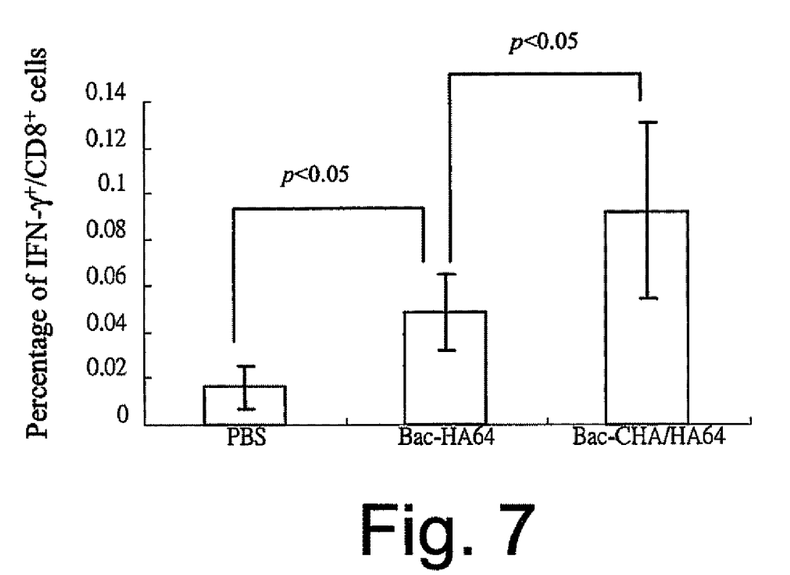
FIG. 7 is a bar chart illustrating the experimental result according to one embodiment of the present invention.

The percentages of IFN-γ secreting CD8+ cells in splenocytes, an indicator of functional cytotoxic T cells responsible for clearing the virus-infected cells, were analyzed by flow cytometry. As illustrated in FIG. 7, Bac-CHA/HA64 elicited statistically higher levels of IFN-γ+/CD8+ splenocytes than those elicited by Bac-HA64 ($p<0.05$). These data confirmed that the baculovirus vectors simultaneously displaying and expressing HA elicited higher levels of functional cytotoxic T cells.

The above-mentioned embodiment may be applied for constructing other baculovirus expression vectors as vaccines. For example, the HA may be replaced by NA for displaying and/or expressing NA to elicit immune response in the host.

In conclusion, the present invention achieves dual functions of (1) subunit vaccine by displaying the influenza surface protein and (2) DNA vaccine by expressing the influenza surface protein. The baculovirus expression vector of the present invention achieves better IgG2a elicitation, hemagglutination inhibition (HI) and cellular immune response via intramuscular injection of the host, compared to conventional arts.

While the invention can be subject to various modifications and alternative forms, a specific example thereof has been illustrated in the drawings and is herein described in details. It should be understood, however, that the invention is not to be limited to the particular form disclosed, but on the contrary, the invention is to cover all modifications, equivalents, and alternatives falling within the spirit and scope of the appended claims.

What is claimed is:

1. A baculovirus expression vector, comprising:
  a first gene cassette configured for displaying a first influenza surface protein onto an envelope of the baculovirus, including
    a first influenza surface protein sequence encoding the first influenza surface protein;
    a baculovirus protein signal sequence operably linked to a 5' end of the first influenza surface protein sequence and encoding a baculovirus signal peptide, wherein the baculovirus signal peptide comprises a membrane localization sequence linked to an N-terminal domain of the first influenza surface protein;
    a baculovirus cytoplasmic domain sequence operably linked to a 3' end of the first influenza surface protein sequence and encoding a baculovirus cytoplasmic domain peptide comprising a membrane anchoring sequence; and
    a first promoter operably linked to the first influenza surface protein sequence and the baculovirus protein signal sequence, wherein the first promoter is a baculovirus promoter; and
  a second gene cassette configured for endogenously expressing a second influenza surface protein and generating immunogenicity in a host comprising a mammalian or an avian, including
    a second influenza surface protein sequence encoding the second influenza surface protein, wherein the first influenza surface comprises a hemagglutinin or a neuraminidase, and the first influenza surface protein and the second influenza surface protein are the same; and
    a second promoter operably linked to the second influenza surface protein sequence, wherein the second promoter is a promoter for the mammalian or the avian.

2. The baculovirus expression vector as claimed in claim 1, wherein the baculovirus protein signal sequence comprises a signal sequence of a gp64 encoding an N-terminal domain signal peptide of the gp64.

3. The baculovirus expression vector as claimed in claim 2, wherein the first gene cassette further comprises a carboxyl terminal domain sequence of a gp64 operably replacing a carboxyl terminal domain sequence of the first influenza surface protein sequence and encoding a carboxyl terminal domain of the gp64 linked to a main domain of the first influenza surface protein.

4. The baculovirus expression vector as claimed in claim 1, wherein the first promoter includes a p10 promoter or a polyhedrin promoter.

5. The baculovirus expression vector as claimed in claim 1, wherein the promoter for the mammalian includes a cytomegalovirus immediate-early promoter, a SV40 promoter, an EF-1α, a CMV early enhancer/chicken β actin (CAG) promoter.

6. The baculovirus expression vector as claimed in claim 1, wherein the promoter for the avian includes a CMV-IE promoter, WSSV promoter (White spot syndrome virus immediate-early promoter one (ie 1)), human alpha-1-anti-trypsin promoter, or SV40 promoter.

* * * * *

SEQUENCE LISTING

```
<160> NUMBER OF SEQ ID NOS: 1

<210> SEQ ID NO 1
<211> LENGTH: 7
<212> TYPE: PRT
<213> ORGANISM: Unknown
<220> FEATURE:
<223> OTHER INFORMATION: baculovirus species

<400> SEQUENCE: 1

Arg Asn Arg Asn Arg Gln Tyr
1               5
```